(12) United States Patent
Khouri

(10) Patent No.: US 11,974,894 B2
(45) Date of Patent: May 7, 2024

(54) ILLUMINATED DENTAL PROP

(71) Applicant: Louie Khouri, Birmingham, MI (US)

(72) Inventor: Louie Khouri, Birmingham, MI (US)

(*) Notice: Subject to any disclaimer, the term of this patent is extended or adjusted under 35 U.S.C. 154(b) by 515 days.

(21) Appl. No.: 17/155,484

(22) Filed: Jan. 22, 2021

(65) Prior Publication Data

US 2021/0220085 A1 Jul. 22, 2021

Related U.S. Application Data

(60) Provisional application No. 62/964,269, filed on Jan. 22, 2020.

(51) Int. Cl.
*A61C 5/90* (2017.01)
*A61B 1/06* (2006.01)
*A61B 1/24* (2006.01)

(52) U.S. Cl.
CPC .............. *A61C 5/90* (2017.02); *A61B 1/0684* (2013.01); *A61B 1/24* (2013.01)

(58) Field of Classification Search
CPC .......... A61C 5/90; A61C 17/10; A61C 1/088; A61B 1/0684; A61B 1/24
USPC ............................. 600/238; 433/93, 138, 140
See application file for complete search history.

(56) References Cited

U.S. PATENT DOCUMENTS

| | | | |
|---|---|---|---|
| 6,332,776 B1 | 12/2001 | Martin et al. | |
| 8,905,924 B2 | 12/2014 | Khouri | |
| 9,095,297 B2 | 8/2015 | Khouri | |
| 9,955,860 B2 | 5/2018 | Khouri | |
| 10,258,438 B2* | 4/2019 | Kang | A61B 5/0088 |
| 2004/0033468 A1* | 2/2004 | Fischer | A61C 5/90 433/140 |
| 2005/0239018 A1* | 10/2005 | Green | A61C 5/90 433/140 |
| 2006/0063129 A1* | 3/2006 | Hirsch | A61C 1/088 433/29 |
| 2010/0291503 A1* | 11/2010 | Shih | A61B 90/16 433/140 |
| 2016/0310234 A1* | 10/2016 | Ritter | A61C 17/08 |
| 2017/0173357 A1* | 6/2017 | Demarest | A61C 19/066 |
| 2018/0368938 A1* | 12/2018 | Parke | A61B 1/24 |
| 2021/0228900 A1* | 7/2021 | Kothari | A61N 5/0603 |

* cited by examiner

*Primary Examiner* — Eduardo C Robert
*Assistant Examiner* — David C Comstock
(74) *Attorney, Agent, or Firm* — Harness, Dickey & Pierce, P.L.C.

(57) ABSTRACT

An illuminated dental prop for holding a patient's mouth open during dental procedures is disclosed. The illuminated dental prop is completely disposed within the patient's mouth during use and includes a bite prop and a lighting assembly that is selectively detachable from the bite prop to allow for intense sterilization of the components before or after use. The lighting assembly is selectively repositionable along the bite prop to accommodate different patient situations. Under certain embodiments of the invention, the body portion and/or the lighting assembly will be disposable after a single use.

16 Claims, 3 Drawing Sheets

ILLUMINATED DENTAL PROP

CROSS-REFERENCE TO RELATED APPLICATIONS

This application claims the benefit of U.S. Provisional Application No. 62/964,269, filed on Jan. 22, 2020. The entire disclosure of the above application is incorporated herein by reference.

BACKGROUND

1. Field of the Invention

The present invention generally relates to illuminated dental props for holding the mouth open during dental procedures. Dental props, per se, are known to come in a variety of shapes and sizes such as wedge-shaped props and C-shaped props by way of non-limiting example. Generally, the props are placed between the upper and lower teeth, opposite the side of the mouth which needs to be accessed by a dental practitioner. However, with regard to accessing and viewing the target area by the dental practitioner, currently available dental props do nothing to enhance the visibility within the oral cavity to carry out the necessary procedure.

Further, while various light sources are available to assist in illuminating the oral cavity, such devices are positioned outside of the oral cavity with the light source directed at the target area. However, external light sources tend to be somewhat ineffective. Thus, the present invention relates to the incorporation of a light assembly with a dental prop of desired size and shape.

2. Description of the Prior Art

Relatively recently a handful of patents and patent applications directed to the general concept of combining a light source with a dental prop have surfaced. One such patent is U.S. Pat. No. 6,332,776 which issued Dec. 6, 2001 to Martin et al. According to one embodiment disclosed, a unitary body formed to include a first cavity having an inclined reflective surface is disclosed. Light projecting from a light source connected to a light conducting cable is projected upon the reflective surface to emit light within the patient's mouth. Under a second embodiment, a dental prop is constructed including a cavity which hosts the lighting elements including a primary induction coil connected to a secondary induction coil. Under all embodiments disclosed, there does not appear to be any teaching or disclosure of a light assembly which is conveniently detachable from the body of the dental prop.

Alternatively, US Patent Publication No. US/2005/0239018 discloses a lighted dental prop wherein the light source is integrated in a permanently fixed relationship with the body of the bite block. Under this scenario, either the entire construction would be discarded after a single use or the product as a whole is sterilized for reuse. There does not appear to be any disclosure as to replacement of the light source if need be which is another apparent design flaw.

A perceived problem with each of the above-referenced teachings is that the light source is not readily removable from the bite block such that the bite block portion can be sterilized or discarded after a single use. Further, the light assembly is either integral with the bite block portion or requires extreme work to detach the same from the bite block.

The present invention has solved many of the foregoing problems with the illuminated dental props set forth in U.S. Pat. Nos. 8,905,924, 9,095,297 and 9,955,860 which are hereby incorporated by reference. Even still, the inventor realized that there is room for improvement. In particular, during certain dental procedures, it would be beneficial to offer a device wherein the light assembly can be positioned such that a majority of the open area which is normally occupied by the light assembly remains open, i.e., unoccupied. It may also be beneficial to provide lighted bite props wherein the light assembly is selectively repositionable within the bite prop housing to modify the lighting array from a wide array to a narrower array. Still other benefits are afforded by the present invention.

SUMMARY

The present invention provides for an illuminated dental prop for holding the dental patient's mouth open during dental procedures which incorporates a selectively detachable light source. In addition to providing much needed light to the oral cavity of a patient, a significant advantage over the above noted references is the ability to readily remove the light assembly from the bite block to facilitate sterilization of the light assembly. The dental props of the present invention are designed to be of a size and geometry to be fully contained within the patient's mouth, i.e., without wires extending out of the mouth, to ensure clearance in the oral cavity of the patient such that the dental practitioner can access the target area with the necessary dental instruments.

The light assembly is selectively attachable at various locations along the open area of the dental prop (rearward). As the light assembly is moved laterally away from the leading edge of the bite prop, more of the open area remains available for access by the dental practitioner, if needed. When in this position the arrangement also has the benefit of pushing the patients cheek outwardly thus creating more working space within the oral cavity. Additionally, as the light assembly is moved away from the leading edge and toward the patients cheek, the light beam can be narrowed and thus, more focused on the opposite side of the patient's mouth.

DRAWINGS

The drawings described herein are for illustration purposes only and are not intended to limit the scope of the present disclosure in any way.

DETAILED DESCRIPTION

Figure 3A:
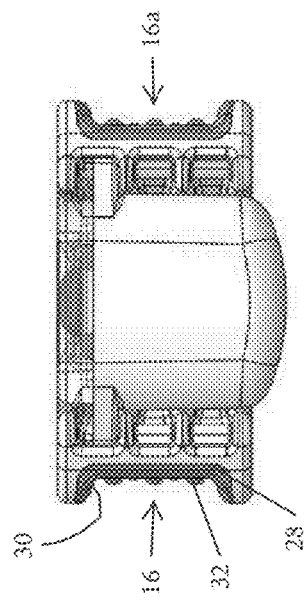
FIGS. 3A-3C are assembled end views of the illuminated dental prop assembly of FIGS. 1 and 2.

The following description is merely exemplary in nature and is not intended to limit the present disclosure, application, or uses. It should be understood that throughout the drawings, corresponding reference numerals indicate like or corresponding parts and features.

Referring to FIGS. 1-5C, there is shown an illuminated dental prop embodiment 10 including two major components, a bite prop 12 and a light assembly 14. The light assembly includes as its main components a housing 18 and a lighting package 20. The housing can be formed from a variety of materials sufficient to protect the lighting package secured within, such as lightweight thermoplastics, thermosets or silicone, by way of non-limiting example. The lighting package typically includes lighting electronics including a circuit board (not shown), battery and switch contacts, a battery 42 and one or more LED lights 62. The lighting assembly is packaged such that the electronics, battery and LED lights are contained therein so that the entire light assembly can be sterilized without risk of damaging the components. Sterilization can be accomplished using ultra-violet radiation, chemical application and/or autoclaving by way of non-limiting example.

As shown, the light assembly housing 18 has an exterior wall 44 defined by a front wall 46, rear wall 48 and opposing top and bottom walls 50, 50a, respectively. Disposed along walls 50 and 50a and the rear wall 48 is a peripheral flange 52. The flange 52 includes recesses 54, 54a generally located near the front wall which receives the tabs 26 projecting from the interior wall of the bite prop. The flange 52 includes wings 56, 56a located proximate to the front wall 46. Optionally, the flange may also include a projection 58 which fits into a pocket 38 located along the interior of the transverse portion. The light assembly may include a translucent cover 60 through which the light generated by the light assembly is transmitted. If the cover is not translucent then the LEDs will extend into cutouts in the cover so as to allow for the free transmission of light. The light assembly will also typically include an on/off button or switch 64 connected to the lighting electronics to allow the battery to energize the LEDs during activation. The switch may be of the type that allows for different levels of activation of the LEDs. For example pressing once one or more of the LEDs are activated, by pressing a second time the LEDs are further activated and a third pressing activates the LEDs still further. This arrangement allows for selectively varying the light intensity, e.g. bright, brighter and brightest.

The bite prop 12 has a substantially C-shaped body including first and second legs, 16 and 16a, respectively, extending at an inclined angle from the transverse portion 22 to define an open area 40 which ultimately is occupied to some extent by the light assembly. This slight angle allows the light assembly to be more easily inserted into the open area 40 for engagement with the bite prop. The bite prop also includes an external wall 28 extending along the transverse portion 22 and first and second legs 16, 16a of the dental prop 10. Optionally, the external wall is recessed along at least the first and second legs thereby providing a trough 30 to preclude lateral movement of the bite prop on the teeth during use. Still further, the trough 30 may be lined, e.g., over-molded, with an elastic material 32 or simply roughened, thereby providing an enhanced tooth-engaging surface. Thus, when the dental prop 10 is positioned over the patient's teeth at the back of the mouth, with the transverse portion near the back and the first and second legs projecting toward the front of the mouth. The extra grip provided along the tooth engaging surface, in association with the patient's natural instinct to close their jaw, helps keep the prop fixed over the teeth.

Figure 3B:
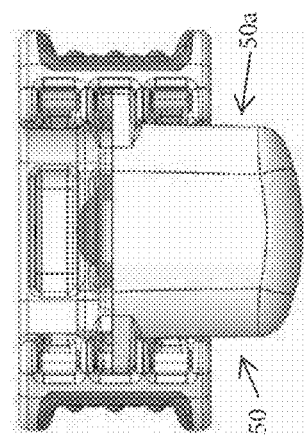
Figure 3C:
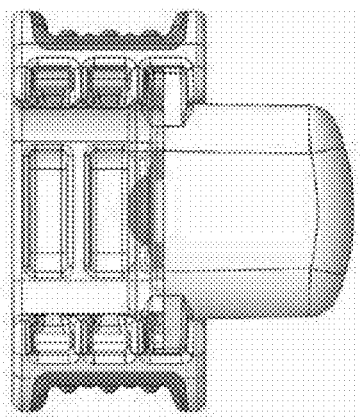
Figure 1:
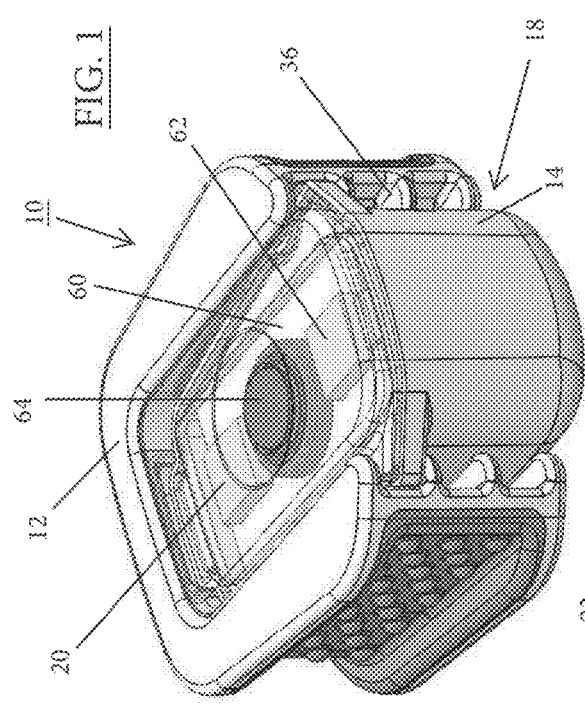
FIG. 1 is a perspective view of a first embodiment of the illuminated dental prop assembly.
Figure 2:
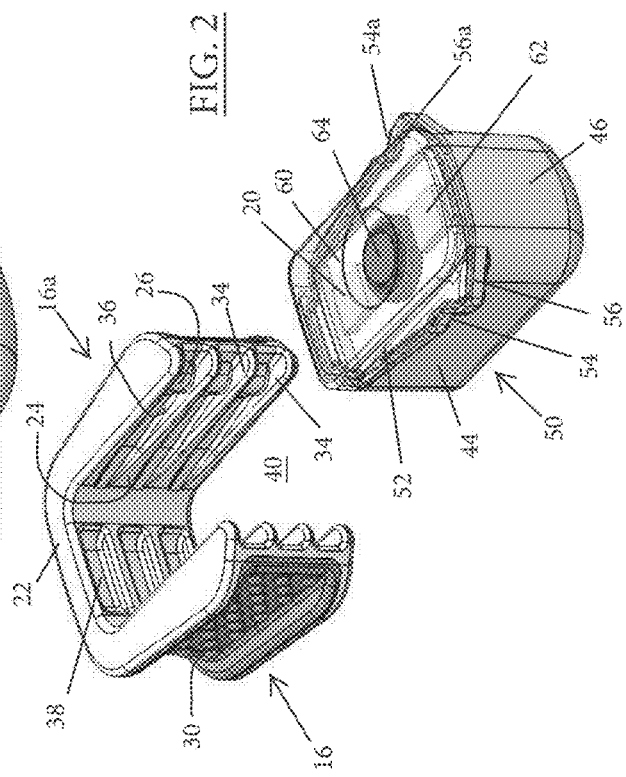
FIG. 2 is a blown apart perspective view of the illuminated dental prop of FIG. 1.
Figure 4:
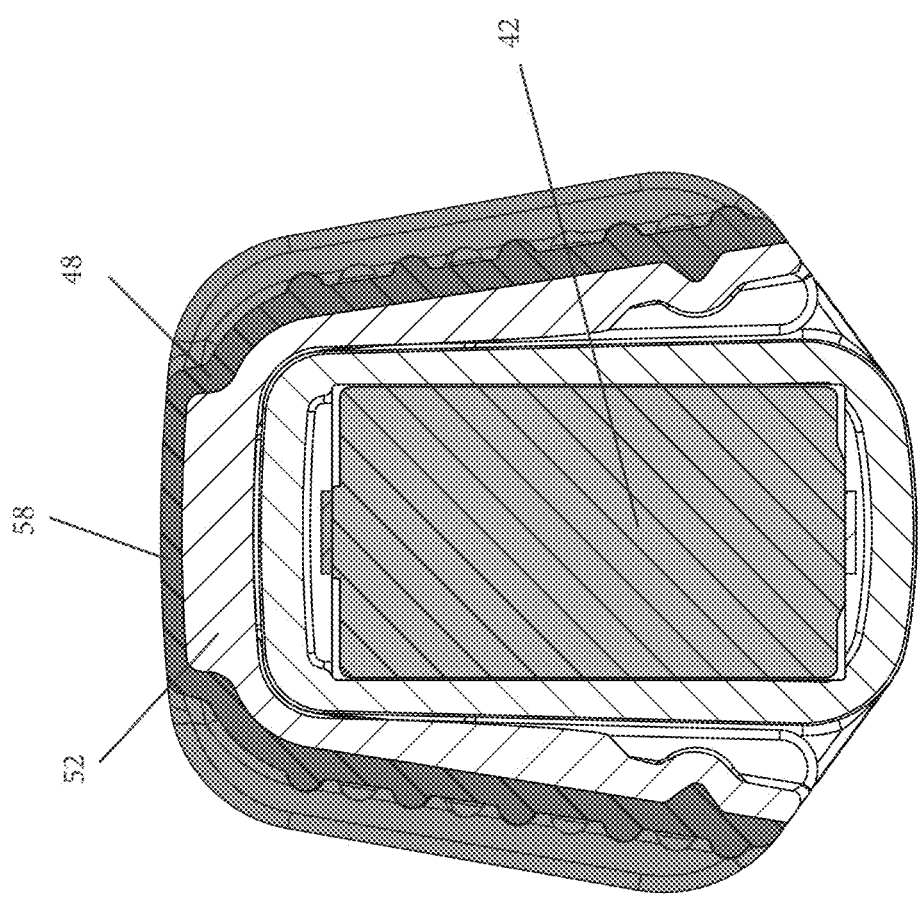
FIG. 4 is a sectional view of the illuminated dental prop of FIGS. 1 and 2.
Figure 5C:
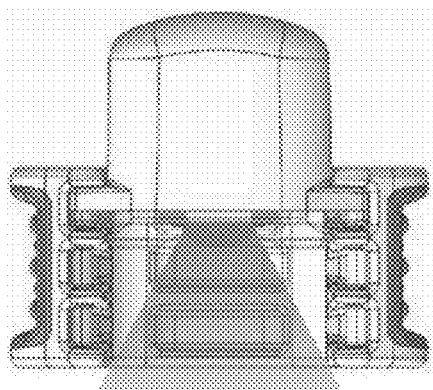
FIGS. 5A-5C are assembled end views demonstrating differing light arrays based on the position of the light assembly relative to the dental prop.
Figure 5B:
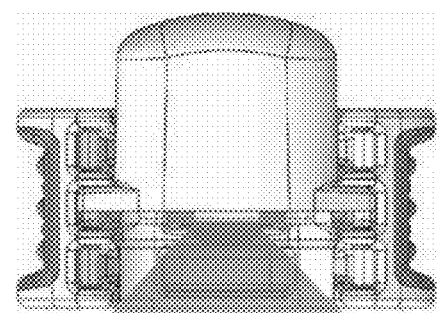
Figure 5A:
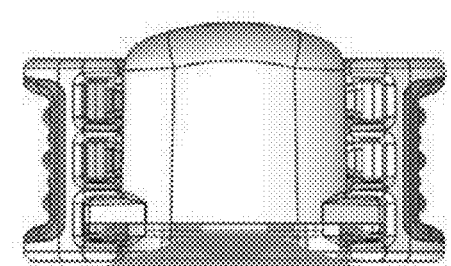

The interior wall 24 of the bite prop which extends along the transverse portion 22 and the first and second legs 16, 16a is sized to tightly accommodate the light assembly 14 when it is fully inserted therein. Projecting inwardly from the interior wall 24 along the first and second legs are a plurality of spaced apart partitions 34 which define slots 36 for hosting the flange 52 of the lighting assembly housing. As shown in FIGS. 3A-3C, the lighting assembly can be repositioned along various locations within the bite prop 12. As further illustrated in FIGS. 5A-5C, when the light assembly is located in the forward position as depicted in FIG. 5A, the light array tends to be widest. In the middle position, the light array is narrowed since the light is somewhat blocked by the first and second legs 16, 16a of the bite prop as shown in FIG. 5B. An even narrower array is provided when the light assembly is positioned in the most reward position. In this position, the light array can be focused in a narrower area along the opposite side of the patient's mouth which, during certain dental procedures, can be useful. As can be appreciated, when the light assembly is located most rearward as shown in FIG. 5C, the area 40 between the first and second legs of the bite prop is largely open which also can be useful if the dental professional needs additional room to work within the oral cavity. Likewise as can be appreciated the housing of the light assembly may push the patients check outwardly to provide more room in the oral cavity.

An enhanced locking feature is also offered by one or more tabs 26 extending from the interior wall 24 which mates with a complementary recess 54, 54a provided along the flange 52 of the light assembly. As shown, it is preferable that there be a tab 26 disposed on each of the first and second legs 16, 16a, between the partitions 34 which can mate with the recess 54, 54a of the flange 52 for additional security of the light assembly to the bite prop. While not shown, it should be understood that the interior wall may have at least one recess and the exterior wall of the light assembly may have one or more locking tabs. As with the light assembly, the bite prop is also sterilisable using an appropriate technique.

The light assembly may include a rechargeable battery via direct charging or using an induction system or may be readily replaceable. Optionally, the light assembly may be replaced with another light assembly when the charge of the battery is exhausted. Under still further embodiments the light assembly housing may be selectively open and closed to replace the battery as needed The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An illuminated dental prop for lighting a patient's mouth comprising:
  a lighting assembly including a housing having an outwardly extending flange and a light source coupled to said housing; and
  a bite prop including a body having a transverse portion and first and second spaced apart legs extending from the transverse portion to define an open area there between, said first and second legs having an inner wall including a plurality of inwardly extending partitions which form a plurality of complimentary slots between said partitions thereby providing multiple locations along which said lighting assembly may be selectively attached to said bite prop, whereby upon inserting the lighting assembly into said bite prop, the outwardly extending flange of the lighting assembly seats within a complimentary slot of said first and second legs to secure the lighting assembly to the bite prop.

2. The illuminated dental prop of claim 1 wherein said bite prop includes at least one inwardly extending tab disposed within a slot which mates with a recess provided along said flange to provide a snap-fit between said lighting assembly and said bite prop.

3. The illuminated dental prop of claim 1 wherein the housing of the lighting assembly is formed from a material selected from the group consisting of thermoplastic, thermosets and silicone.

4. The illuminated dental prop of claim 1 wherein the housing of the lighting assembly includes a translucent portion through which light generated by the at least one light source is transmitted.

5. The illuminated dental prop of claim 1 wherein the bite prop is substantially C-shaped.

6. The illuminated dental prop of claim 1 wherein the lighting assembly further comprises a battery, a circuit board and an activation switch.

7. The illuminated dental prop of claim 1 wherein the light intensity of the light source can be varied.

8. The illuminated dental prop of claim 1 wherein the light source includes one or more light emitting diodes (LEDs).

9. The illuminated dental prop of claim 1 wherein the lighting assembly is sterilisable.

10. The illuminated dental prop of claim 1 wherein the bite prop is sterilisable.

11. The illuminated dental prop of claim 1 wherein said light source is contained within said housing.

12. The illuminated dental prop of claim 1 wherein said light source generates a light array.

13. The illuminated dental prop of claim 12 wherein intensity of the light source can be adjusted.

14. The illuminated dental prop of claim 1 wherein the body of the bite prop includes an external wall along said transverse portion and said first and second legs.

15. The illuminated dental prop of claim 14 wherein the external wall of said first and second legs includes a trough.

16. The illuminated dental prop of claim 15 wherein the troughs include an over-molded material.

* * * * *